US006630569B1

(12) United States Patent
Jeschke et al.

(10) Patent No.: US 6,630,569 B1
(45) Date of Patent: Oct. 7, 2003

(54) ECTOPARASITICIDE AGENTS

(75) Inventors: Peter Jeschke, Gladbach (DE); Andreas Turberg, Haan (DE); Norbert Mencke, Leverkusen (DE); Olaf Hansen, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/719,626

(22) PCT Filed: Jun. 11, 1999

(86) PCT No.: PCT/EP99/04029

§ 371 (c)(1),
(2), (4) Date: Dec. 14, 2000

(87) PCT Pub. No.: WO99/66794

PCT Pub. Date: Dec. 29, 1999

(30) Foreign Application Priority Data

Jun. 24, 1998 (DE) .......................... 198 28 043

(51) Int. Cl.[7] .................................. C07K 7/50
(52) U.S. Cl. .................. 530/317; 530/328; 514/11; 514/16
(58) Field of Search ................ 530/317, 328; 514/11, 16

(56) References Cited

U.S. PATENT DOCUMENTS 5,514,773 A  5/1996  Nishiyama et al. ......... 530/317

FOREIGN PATENT DOCUMENTS

WO  97/09331  3/1997

OTHER PUBLICATIONS

Potts J Postgraduate Medicine 110 (1) 57–99 and 63–64, 2001.*
Taylor M A Veterinary Journal 161 (3) 253–268, 2001.*
Levot, G. W. International Journal for Parasitology 25 (11) 1355–62, 1995.*
Brown S Clinical Infectious Diseases 20, Suppl 1, S104–9, 1995.*
Burns D. A. British Journal of Dermatology 125 (2) 89–93, 1991.*
Kunkle, G. Journal of Veterinary Pharmacology and Therapeutics, vol. 20, (suppl. 1), pp. 110–112, 1997.*
Zunke, U. Revue de Nematologie, 1990. vol. 13, No. 3. p. 331–337.*
Cooke, D.A. Crop protection, vol. 8, No. 1. p. 63–70, 1989.*
Hopla Revue Scientifique et Technique 13, 985–1017 1994.*
Agric.Biol. Chem., 43(5), (month unavailable) 1979, pp. 1079–1083, Masaharu Kanaoka, Akira Isogal and Akinori Suzuki, Syntheses of Bassianolide and Its Two Homologs, Enniatin C and Decabassianolide.
Patent Abstracts of Japan, vol. 18, No. 46, Jan. 25, 1994 & JP 05 271013 A (Meiji Seika Kaisha) Oct. 19, 1993.

* cited by examiner

Primary Examiner—Christopher S. F. Low
Assistant Examiner—David Lukton
(74) Attorney, Agent, or Firm—Susan M. Pellegrino

(57) ABSTRACT

The present invention relates to the ectoparasiticidal use of cyclic depsipeptides of the formula (I)

(I)

in which
$R^1$, $R^2$, $R^3$, $R^4$, $X^1$, $X^2$, $X^3$ and $X^4$ are substituents described herein, which are effective for controlling ectoparasites, and to ectoparasiticidal compositions containing the depsipeptides.

8 Claims, No Drawings

ECTOPARASITICIDE AGENTS

The present invention relates to the use of cyclic depsipeptides, in particular 24-membered cyclodepsipeptides, for controlling ectoparasites, and to ectoparasiticidal compositions which comprise the depsipeptides.

Cyclic depsipeptides, and their preparation and use as parasiticides against helminths, nematodes and trematodes in animals (endoparasiticides) have already been the subject of numerous publications.

Known is, for example, a cyclodepsipeptide with the name PF 1022A and its action against endoparasites (EP-A 382 173 and EP-A 503 538). Further cyclic depsipeptides (cyclooctadepsipeptides: WO 98/55 469; WO 98/43 965; WO 93/19 053; EP-A 634 408; WO 94/19 334; WO 95/07 272; EP-A 626 375; EP-A 626 376; EP-A 664 297; EP 634 408; EP-A 718 298; WO 97/09 331; cyclohexadepsipeptides: WO 93/25 543; WO 95/27 498; EP-A 658 551; cyclotetradepsipeptides: EP-A 664 297; dioxomorpholines: WO 96/38 165: JP 08 225 552) and open-chain depsipeptides (EP-A 657 171; EP-A 657 172; EP-A 657 173; WO 97/07 093) and their endoparasiticidal action have been described.

Furthermore, it is already known that certain 24-membered cyclodepsipeptides, for example bassianolide and PF1022A, have insecticidal activity against silkworms (cf. M. Kanaoka et al., Agric. Biol. Chem. 43 (5), 1979, pp. 1079–83; JP 05 271 013).

However, the insecticidal activity of the prior-art compounds is, in particular at low application rates and concentrations, not entirely satisfactory in all areas of use. Futhermore, their use against ectoparasites, for example ticks, fleas and mites, has hitherto not been disclosed.

The present application provides:

Method of use of cyclooctadepsipeptides of the formula (I)

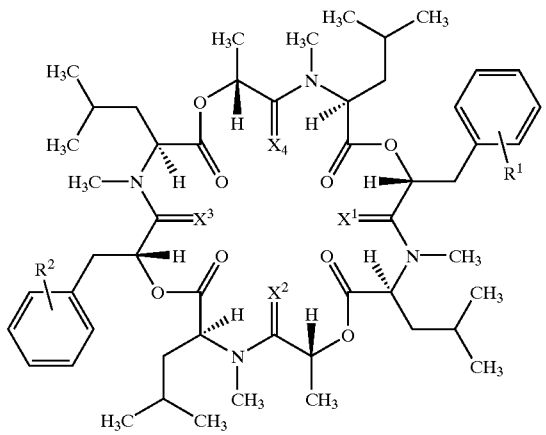

in which $R^1$ represents hydrogen, $C_{1-4}$-alkyl, in particular methyl, hydroxyl, halogen, in particular fluorine, $C_{1-4}$-alkoxy, in particular methoxy or tert-butyloxy, $C_{1-4}$-alkoxy-$C_{1-4}$-alkyl, in particular methoxymethyl, ethoxyethyl, heterocyclylmethyl, in particular pyridylmethyl, tetrahydrofuranylmethyl, pyrrolidinylmethyl, furylmethyl, thienylmethyl, heteroaryl-$C_{1-2}$-alkoxy, in particular pyridyl-methoxy, tetrahydrofuryl-methoxy, pyrrolidinyl-methoxy and furyl-methoxy, nitro, —$NR^3R^4$, —$SO_2$—$NR^3R^4$, $R^2$ represents hydrogen, $C_{1-4}$-alkyl, in particular methyl, hydroxyl, halogen, in particular fluorine, $C_{1-4}$-alkoxy, in particular methoxy or tert-butyloxy, $C_{1-4}$-alkoxy-$C_{1-4}$-alkyl, in particular methoxymethyl, ethoxyethyl, heterocyclylmethyl, in particular pyridylmethyl, tetrahydrofuranylmethyl, pyrrolidinylmethyl, furylmethyl, thienylmethyl, heteroaryl-$C_{1-2}$-alkoxy, in particular pyridyl-methoxy, tetrahydrofuranyl-methoxy, pyrrolidinyl-methoxy and furyl-methoxy, nitro, —$NR^3R^4$, —$SO_2$—$NR^3R^4$, $R^3$ and $R^4$ independently of one another each represent hydrogen, optionally substituted $C_{1-4}$-alkyl, formyl, $C_{1-4}$-alkoxycarbonyl, optionally substituted arylmethyl, in particular benzyl, or heterocyclylmethyl, in particular pyridylmethyl, tetrahydrofuranylmethyl, pyrrolidinylmethyl, furylmethyl, thienylmethyl, $R^3$ and $R^4$ together with the nitrogen atom to which they are attached represent an optionally substituted mono- or polycyclic, optionally bridged and/or spirocyclic, saturated or unsaturated heterocycle which may contain one to three further heteroatoms from the group consisting of nitrogen, oxygen and sulphur, $X^1$, $X^2$, $X^3$ and $X^4$ independently of one another represent oxygen or sulphur, where, if $R^1$ and $R^2$ simultaneously represent hydrogen, at least one of the radicals $X^1$, $X^2$, $X^3$ and $X^4$ represents sulphur.

Depending on the nature of the substituents, the compounds of the general formula (I) can be present as geometrical and/or optical isomer mixtures of varying compositions. The invention relates both to the pure isomers and to the isomer mixtures.

The formula (I) provides a general definition of the cyclooctadepsipeptides which can be used according to the invention.

The substituents $R^1$ and $R^2$ are preferably in the para- or ortho-position. Particular preference is given to the para-position.

The substituents $X^1$, $X^2$ and $X^3$ preferably represent oxygen, the substituent X4 preferably represents oxygen or sulphur.

Compounds of the general formula (I) which can be used according to the invention and which may be mentioned are, in particular, the compounds of the formula (II) below known from the PCT applications WO 93/19 053, WO 97/11 064 and EP-A 634 408 A1:

(II)

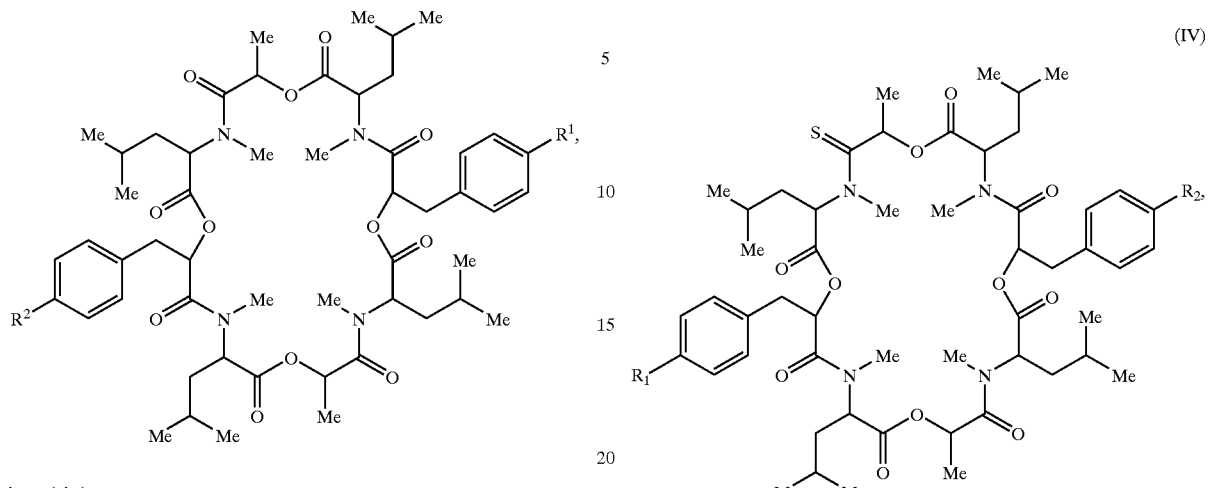

(IV)

in which
R¹ and R² represent identical or different radicals from the group consisting of hydrogen, N-morpholino, nitro, amino, mono- and dimethylamino, furylmethoxy, tetrahydrofurylmethoxy, pyrrolidinylmethoxy or pyridylmethoxy, but do not simultaneously represent hydrogen.

Furthermore, mention may be made of the compounds known from the PCT application WO 94/19 334.

Particular mention may be made of the compounds, known from the PCT applications WO 94/19 334 and WO 97/11 064, of the formula (III) below (III)

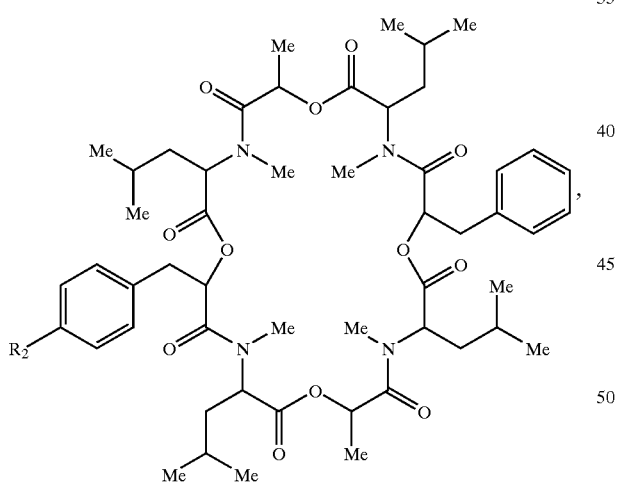

in which
R² represents hydroxy, methoxy or tert-butoxy and furylmethoxy.

Finally, mention may be made of the prior-art compounds known from the PCT application WO 95/07 272.

The generic formulae and definitions described in these publications, and the individual compounds described therein, are explicitely incorporated herein by way of reference.

Furthermore and in particular, as compounds of the general formula (I) which can be used according to the invention and in which at least one of the substituents $X^1$, $X^2$ and $X^3$ and/or $X^4$ represents sulphur, mention may be made of the cyclic depsipeptides of the general formula (IV) and (V):

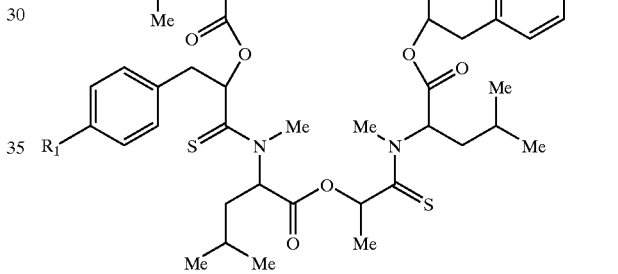

(V)

in which
R¹ and R² represent identical or different radicals from the group consisting of hydrogen. N-morpholino, nitro, amino, mono- and dimethylamino, furylmethoxy, tetrahydrofurylmethoxy, pyrrolidinomethoxy or pyridylmethoxy.

The cyclic depsipeptides of the general formula (IV) and (V) form part of the subject-matter of a patent application of the applicant, which is a prior publication (cf. WO 98/43 965). These compounds are prepared by thionating compounds of the formula (I) in which $X^1$, $X^2$ and $X^3$ and $X^4$ represent oxygen with a suitable sulphurizing agent in the presence of diluent. Reference is made here to the corresponding Preparation Examples further below.

The cyclic depsipeptides which can be used according to the invention are suitable for controlling animal pests, such as arthropods, preferably insects, arachnids, encountered in animal husbandry and livestock breeding, in productive livestock, breeding stock, zoo animals, laboratory animals, animals used in experiments and pets, and have low toxicity toward warm-blooded animals. They are active against all or some stages of development of the pests and against resistant and normally sensitive species of the pests.

By controlling the animal pests, it is intended to prevent diseases and their transmission, mortality and decreasing performance (for example in the production of meat, milk, wool, hides, eggs), so that more economical and simpler animal keeping is possible, or so that in certain areas animal keeping is possible at all, by using the active compounds.

The pests include:

from the order of the Anoplura, for example, Haematopinus spp., Linognathus spp., Solenopotes spp., Pediculus spp., Pthirus spp.;

from the order of the Mallophaga, for example, Trimenopon spp., Menopon spp., Eomenacanthus spp., Menacanthus spp., Trichodectes spp., Felicola spp., Damalinea spp., Bovicola spp.;

from the order of the Diptera, for example, Chrysops spp., Tabanus spp., Musca spp., Hydrotaea spp., Muscina spp., Haematobosca spp., Haematobia spp., Stomoxys spp., Fannia spp., Glossina spp., Lucilia spp., Calliphora spp., Auchmeromyia spp., Cardylobia spp., Cochiomyia spp., Chrysomyia spp., Sarcophaga spp., Wohlfartia spp., Gasterophilus spp., Oesteromyia spp., Oedemagena sp., Hypoderma spp., Oestrus spp., Rhinoestrus spp., Melophagus spp., Hippobosca spp.

from the order of the Siphonaptera, for example, Ctenocephalides spp., Echidnophaga spp., Ceratophyllus spp.

from the order of the Metastigmata, for example, Hyalomma spp., Rhipicephalus spp., Boophilus spp., Amblyomma spp., Haemophysalis spp., Dermacentor spp., Ixodes spp., Argas spp., Ornithodorus spp., Otobius spp.;

from the order of the Mesostigmata, for example, Dermanyssus spp., Ornithonyssus spp., Pneumonyssus spp.

from the order of the Prostigmata, for example, Cheyletiella spp., Psorergates spp., Myobia spp., Demodex spp., Neotrombicula spp.;

from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptex spp., Cytodites spp., Laminosioptes spp.

The livestock and breeding stock include mammals, such as, for example, cattle, sheep, goats, horses, pigs, dogs, cats, camels, water buffalo, donkeys, rabbits, fallow deer, reindeer, fur-bearing animals, such as, for example, minks, chinchilla or racoon, birds, such as, for example chickens, turkeys, pheasants, geese, ducks.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, suppositories, tablets, capsules, drinks, granules, drenches, boluses, medicated feed or drinking water. Dermal application is effected, for example, in the form of dipping, spraying, bathing, washing, pouring-on and spotting-on, rubbing-in and powdering. Parenteral administration is effected, for example, in the form of injection (intramuscular, subcutaneous, intravenous or intraperitoneal) or by implants.

Suitable preparations include:

solutions, such as solutions for injection, oral solutions, concentrates for oral administration after dilution, solutions for use on the skin or in body cavities, pour-on formulations, gels;

emulsions and suspensions for oral or dermal administration and for injection; semi-solid preparations;

formulations in which the active compound is incorporated in a cream base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl alcohol, glycerol, hydrocarbons, propylene glycol, polyethylene glycols and N-methylpyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on, or applied by dipping, bathing or washing. These solutions are prepared as described above in the case of the solutions for injection.

It may be advantageous to add thickeners in the preparation process. The following are thickeners: inorganic thickeners, such as bentonites, colloidal silica, aluminium monostearate, or organic thickeners, such as cellulose derivatives, polyvinyl alcohols and their copolymers, acrylates and metacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically or distributing itself over the surface of the body.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethyl acetamide, N-methylpyrrolidone, or 2-dimethyl-4-oxy-methylene-1,3-dioxolane.

Colorants are all colorants which can be dissolved or suspended and which are approved for use in animals.

Examples of bioabsorption promoters are DMSO, spreading oils, such as isopropyl myristate, dipropylene glycol pelargonate, silicone oils, fatty acid esters, triglycerides or fatty alcohols.

The following are antioxidants: sulphites or metabisulphites, such as potassium metabisulphite, ascorbic acid, butylhydroxytoluene, butylhydroxyanisole or tocopherol.

Examples of photostabilizers are substances from the class of the benzophenones or novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, bioabsorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck uropygial fat, dibutyl phthalate, diIsopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include:

water, alcohols, such as, for example, propylene glycol, glycerol, sorbitol and their mixtures.

Suitable emulsifiers include:

nonionic surfactants, for example polyethoxylated castor oil, polyethoxylated sorbitan monooleate, sorbitan monostearate, glycerol monostearate, polyethoxy stearate or alkylphenol polyglycol ethers;

ampholytic surfactants, such as disodium N-lauryl-β-iminodipropionate or lecithin;

anionic surfactants, such as Na lauryl sulfate, fatty alcohol ether sulphates, and the monoethanolamine salt of mono/dialkylpolyglycol ether orthophosphoric ester;

cationic surfactants, such as cetyltrimethylammonium chloride.

Other suitable auxiliaries include: substances which increase the viscosity and stabilize the emulsion, such as carboxymethylcellulose, methylcellulose and other cellulose and starch derivatives, polyacrylates, alginates, gelatin, gum arabic, polyvinyl-pyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, bioabsorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminium oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds.

Ready-to-use preparations contain the active compound in concentrations of 10 ppm to 20% by weight, preferably from 0.1 to 10% by weight.

Preparations which are diluted before use contain the active compound in concentrations of 0.5 to 90% by weight, preferably from 5 to 50% by weight.

In general, it has been found to be advantageous to administer amounts of about 1 to 100 mg of active compound per kg of bodyweight per day to obtain effective results.

Suitable examples of formulations of the depsipeptides which can be used according to the invention are given below, without the invention being limited in any way:

EXAMPLES

Example 1

SC-(Suspension concentrate) formulation:
368 g of active compound of the formula (I)
35 g of block polymer of emulsifier ethylene oxide- and propylene oxide
12 g of ditolyl ether sulphonate/formaldehyde condensate (emulsifier)
3.5 g of water-soluble polyvinyl alcohol
58.0 g of $NH_4Cl$
116.0 g of urea
1.2 g of (37% strength aqueous hydrocloric acid)
4.6 g of gum xanthan
560.5 g of distilled water

Example 2

WP (dispersible powder) formulation:
25.0 g of active compound of the formula (I)
1.0 g of diisobutyl-naphthalene Na sulphonate
10.0 g of n-dodecylbenzylsulphonic acid calcium
12.0 g of finely divided silica-containing alkylaryl polyglycol ether
3.0 g of ditolyl ether sulphonate/formaldehyde condensate (emulsifier)
2.0 g of ®Baysilon-E, a silicon-containing antiform by Bayer AG
2.0 g of finely divided silica and
45.0 g of kaolin

Example 3

SL-(water-soluble concentrate) formulation
18.3 g of active compound of the formula (I)
2.5 g of neutral emulsifier, based on alkylaryl polyglycol ether
3.5 g of sodium diisooctyl sulphosuccinate
38.4 g of dimethyl sulphoxide
37.5 g of 2-propanol

Example 4

SL-(water-soluble concentrate) formulation
185. [lacuna] g of active compound of the formula (I)
5.0 g of sodium diisooctyl sulphosuccinate and
76.5 g of dimethyl sulphoxide
are mixed into a 100 g shampoo formulation consisting of
  44.4% by weight of Marion AT 50, a triethanolamine salt of alkylbenzene sulphonic acids, from Hüls AG
  11.1% by weight of Marion A 350, sodium salt of alkylbenzene sulphonic acids, from Hüls AG
  3.0% by weight of a condensate of oleic acids and diethanolamine, from Hüls AG and
  41.5% by weight of polyethylene glycol.

Example 5

Spray formulation consisting of
2.0 g of active compound of the formula (I)
10.0 g of dimethyl sulphoxide
35.0 g of 2-propanol and
53.0 g of acetone Hereinbelow, some preparation examples are given for compounds of the formula (I) in which $X^1$, $X^2$, $X^3$ and/or $X^4$ represent sulphur:

Example 6

Cyclo(-N-methyl-L-leucinyl-D-thiolactyl-N-methyl-L-leucinyl-D-phenylthiolactyl-N-methyl-L-leucinyl-D-thiolactyl-N-methyl-L-leucinyl-D-phenylthiolactyl-)

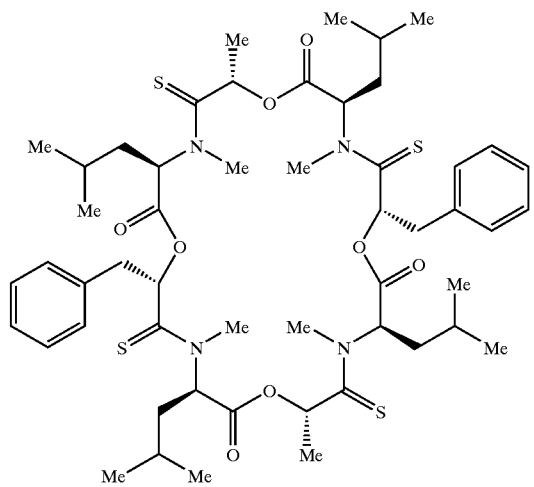

1.0 g (1.05 mmol) of cyclo(-N-methyl-L-leucinyl-D-lactyl-N-methyl-L-leucinyl-D-phenyllactyl-N-methyl-L-leucinyl-D-lactyl-N-methyl-L-leucinyl-D-phenyllactyl-) PF 1022A (cf. EP-A 382 173, U.S. Pat. No. 5,116,815) in 20 ml of toluene was admixed with 1.4 g (3.5 mmol) of 2,4-bis-(4-methoxy-phenyl)-2,4-dithioxo-1,3,2,4-dithiadiphosphetan ("Lawesson's Reagent") and stirred at reflux temperature for 3.5 hours. The entire reaction mixture is then cooled to 0° C. and filtered, and the filtrate obtained is concentrated under reduced pressure. The crude product obtained is chromatographed over a silica gel column (silica gel 60-Merck, particle size: 0.04 to 0.063 mm), eluting first with methylene chloride and then with cyclohexane:acetone (3:1). 0.46 g (43.6% of theory) of cyclo(-N-methyl-L-leucinyl-D-thiolactyl-N-methyl-L-leucinyl-D-phenylthiolactyl-N-methyl-L-leucinyl-D-thiolactyl-N-methyl-L-leucinyl-D-phenylthiolactyl-) are obtained.

$^1$H NMR (CDCl$_3$, δ): 2.99, 3.06, 3.26, 3.42 (4×—N-Me); 4.86, 6.42, 6.61 (4×—N—CH$_2$—); 5.31, 5.55, 5.81, 5.89 (4×—O—CH$_2$—); 7.26 (phenyl-H) ppm.

LC-MS (acidic) m/z (%): 1013 (M$^+$, 100); 310 (21); 274 (30); 198 (42).

C$_{52}$H$_{76}$N$_4$O$_8$S$_4$ (1013.4)

Example 7

Cyclo(-N-methyl-L-leucinyl-D-thiolactyl-N-methyl-L-leucinyl-D-4-nitro-phenyl-thiolactyl-N-methyl-L-leucinyl-D-thiolactyl-N-methyl-L-leucinyl-D-4-nitro-phenylthiolactyl-)

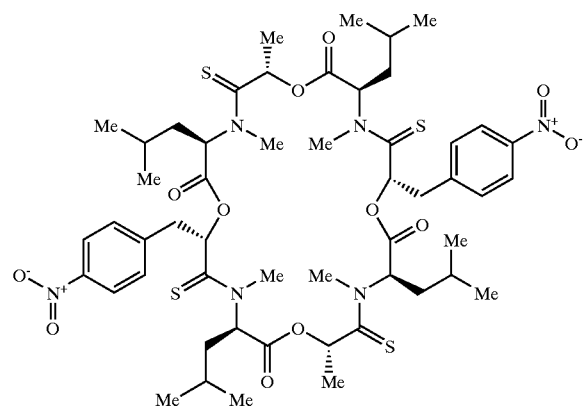

The thionation is carried out similarly to the reaction procedure of Example 1, using:

0.50 g (0.48 mmol) of cyclo(-N-methyl-L-leucinyl-D-lactyl-N-methyl-L-leucinyl-D-4-nitro-phenyllactyl-N-methyl-L-leucinyl-D-lactyl-N-methyl-L-leucinyl-D-4-nitro-phenyllactyl-) (cf. WO 93/19 053, EP-A 634 408)

0.65 g (1.59 mmol) of 2,4-bis-(4-methoxy-phenyl)-2,4-dithioxo-1,3,2,4-dithiadiphosphetan ("Lawesson's Reagent")

10 ml of absolute toluene

The crude product obtained is chromatographed over a silica gel column (silica gel 60-Merck, particle size: 0.04 to 0.063 mm), eluting first with methylene chloride and then with cyclohexane:acetone (3:1). 0.34 g (63.8% of theory) of cyclo(-N-methyl-L-leucinyl-D-thiolac-tyl-N-methyl-L-leucinyl-D-4-nitro-phenylthiolactyl-N-methyl-L-leucinyl-D-thiolactyl-N-methyl-L-leucinyl-D-4-nitro-phenylthiolactyl-) is obtained.

$^1$H NMR (CDCl$_3$, δ): 3.04, 3.09, 3.25, 3.50 (4×—N-Me); 4.87, 6.38, 6.56, 6.63 (4×—N—CH$_2$—); 5.31, 5.52, 5.81, 5.91 (4×—O—CH$_2$—), 8.17, 7.46 (aryl-H) ppm.

LC-MS (acidic) m/z (%): 1103 (M+H, 100); 392 (38); 177 (40); 136 (30).

C$_{52}$H$_{74}$N$_6$O$_{12}$S$_4$ (1103.4)

Example 8

Cyclo(-N-methyl-L-leucinyl-D-thiolactyl-N-methyl-L-leucinyl-D-4-N-morpholino-phenylthiolactyl-N-methyl-L-leucinyl-D-thiolactyl-N-methyl-L-leucinyl-D-4-N-morpholino-phenylthiolactyl-)

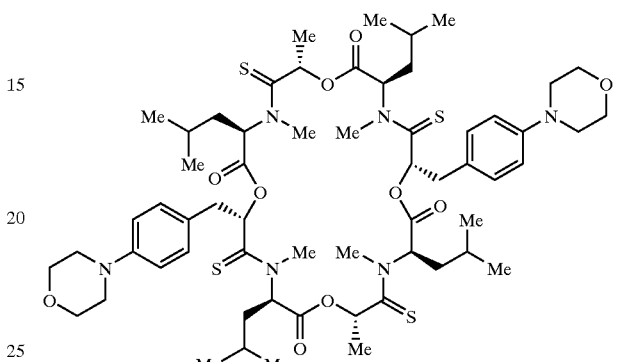

The thionation is carried out similarly to the reaction procedure of Example 1, using:

0.50 g (0.44 mmol) of cyclo (-N-methyl-L-leucinyl-D-lactyl-N-methyl-L-leucinyl-D-4-N-morpholino-phenyllactyl-N-methyl-L-leucinyl-D-lactyl-N-methyl-L-leucinyl-D-4-N-morpholino-phenyllactyl-) (cf. WO 93/19 053, EP-A 634 408)

0.60 g (1.48 mmol) of 2,4-bis-(4-methoxy-phenyl)-2,4-dithioxo-1,3,2,4-dithiadiphosphetan ("Lawesson's Reagent")

10 ml of absolute toluene

The crude product obtained is chromatographed over a silica gel column (silica gel 60-Merck. particle size: 0.04 to 0.063 mm), eluting first with methylene chloride and then with cyclohexane:acetone (3:1). 0.37 g (70.0% of theory) of cyclo(-N-methyl-L-leucinyl-D-thio-lactyl-N-methyl-L-leucinyl-D-4-N-morpholino-phenylthiolactyl-N-methyl-L-leucinyl-D-thiolactyl-N-methyl-L-leucinyl-D-4-N-morpholino-phenylthiolactyl-) is obtained.

$^1$H NMR (CDCl$_3$, δ): 3.01, 3.08, 3.26, 3.40 (4×—N-Me); 3.12, 3.85 (2×Mor); 4.85, 6.42, 6.62 (4×—N—CH$_2$—); 5.30, 5.55, 5.78, 5.88 (4×—O—CH$_2$—); 6.81, 7.26 (aryl-H) ppm.

Example 9

Cyclo-(N-methyl-L-leucinyl-D-thiolactyl-N-methyl-L-leucinyl-D-4-morpholino-phenyllactyl-N-methyl-L-leucinyl-D-lactyl-N-methyl-L-leucinyl-D-4-N-morpholinophenyllactyl-)

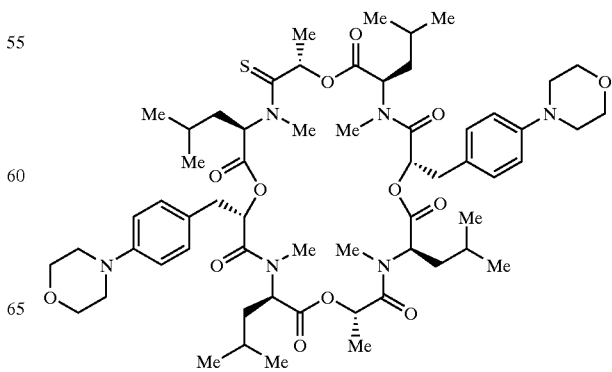

The thionation is carried out similarly to the reaction procedure of Example 7, using:

0.41 g (0.37 mmol) of cyclo(-N-methyl-L-leucinyl-D-lactyl-N-methyl-L-leucinyl-D-4-N-morpholino-phenyllactyl-N-methyl-L-leucinyl-D-lactyl-N-methyl-L-leucinyl-D-4-N-morpholino-phenyllactyl-) (cf. WO 93/19 053, EP-A 634 408)

0.36 g (0.73 mmol) of 2,4-bis-(4-phenoxy-phenyl)-2,4-dithioxo-1,3,2,4-dithiadiphosphetan ("Belleau's Reagent")

10 ml of absolute toluene

The crude product obtained is chromatographed over a silica gel column (silica gel 60-Merck, particle size: 0.04 to 0.063 mm), eluting with cyclohexane:acetone (3:1). 0.70 g (16.8% of theory) of cyclo(-N-methyl-L-leucinyl-D-thiolactyl-N-methyl-L-leucinyl-D-4-N-morpholino-phenyllactyl-N-methyl-L-leucinyl-D-lactyl-N-methyl-L-leucinyl-D-4-N-morpholino-phenyllactyl-) is obtained.

LC-MS (acidic) m/z (%): 1135 (M$^+$, 56); 361 (100).

$C_{60}H_{90}N_6O_{13}S$ (1135.4)

$R_t$ (HLPLC): 16.53 min.

Example 10

Cyclo(-N-methyl-L-leucinyl-D-thiolactyl-N-methyl-L-leucinyl-D-4-nitro-phenyllactyl-N-methyl-L-leucinyl-D-lactyl-N-methyl-L-leucinyl-D-4-nitro-phenyllactyl-)

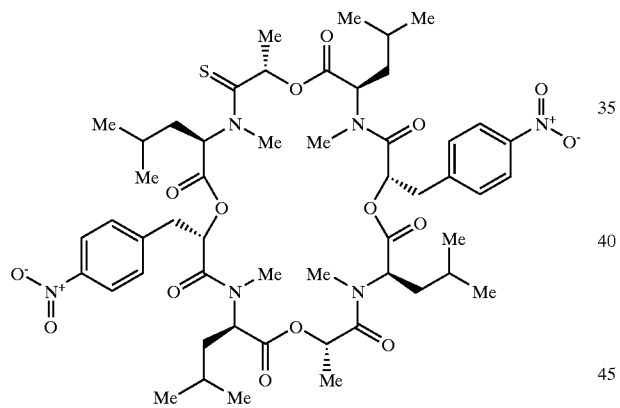

The thionation is carried out similarly to the reaction procedure of Example 7, using:

0.50 g (0.48 mmol) of cyclo(-N-methyl-L-leucinyl-D-lactyl-N-methyl-L-leucinyl-D-4-nitro-phenyllactyl-N-methyl-L-leucinyl-D-lactyl-N-methyl-L-leucinyl-D-4-nitro-phenyllactyl-) (cf. WO 93/19 053, EP-A 634 408)

0.24 g (0.48 mmol) of 2,4-bis-(4-phenoxy-phenyl)-2,4-dithioxo-1,3,2,4-dithiadiphosphetan ("Belleau's Reagent")

10 ml of absolute tetrahydrofuran

The reaction mixture is stirred at 50° C. for 24 hours and concentrated under reduced pressure. The crude product obtained is chromatographed over a silica gel column (silica gel 60-Merck, particle size: 0.04 to 0.063 mm), eluting with cyclohexane:acetone (4:1). The product is then purified again using preparative HPLC (gradient:water/acetonitrile). 16 mg (3.1% of theory) of cyclo(-N-methyl-L-leucinyl-D-thiolactyl-N-methyl-L-leucinyl-D-4-nitro-phenyllactyl-N-methyl-L-leucinyl-D-lactyl-N-methyl-L-leucinyl-D-4-nitro-phenyllactyl-) are obtained.

LC-MS (acidic) m/z (%): 1056 (M+H, 38).

$C_{52}H_{74}N_6O_{15}S$ (1055.3)

$R_t$ (HPLC): 17.38 min.

Example 11

Cyclo(-N-methyl-L-leucinyl-D-thiolactyl-N-methyl-L-leucinyl-D-4-(pyrid-2-yl-methoxy)-phenyllactyl-N-methyl-L-leucinyl-D-lactyl-N-methyl-L-leucinyl-D-4-(pyrid-2-yl-methoxy)-phenyllactyl-)

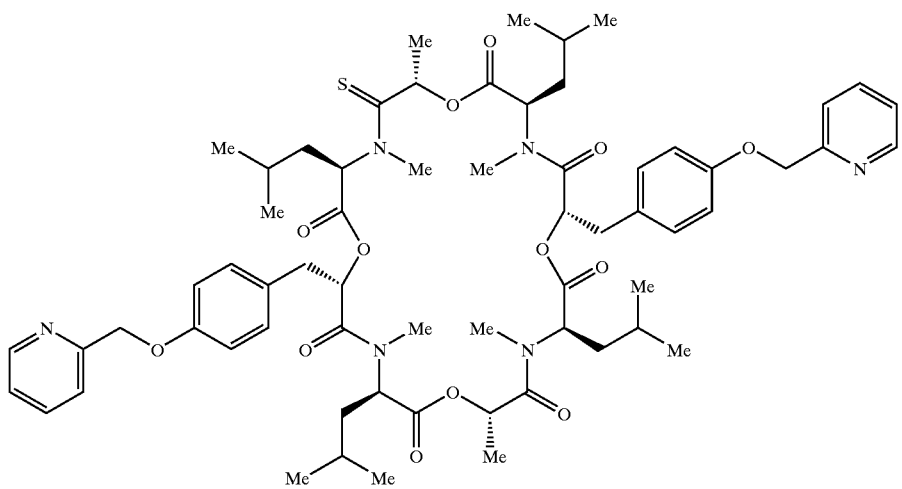

The thionation is carried out similarly to the reaction procedure of Example 9. using:

- 0.41 g (0.35 mmol) of cyclo(-N-methyl-L-leucinyl-D-lactyl-N-methyl-L-leucinyl-D-4-(pyrid-2-yl-methoxy)-phenyllactyl-N-methyl-L-leucinyl-D-lactyl-N-methyl-L-leucinyl-D-4-(pyrid-2-yl-methoxy)-phenyllactyl-) (cf. WO 97/11 064)
- 0.57 g (1.41 mmol) of 2,4-bis-(4-methoxy-phenyl)-2,4-dithioxo-1,3,2,4-dithiadiphosphetan ("Belleau's Reagent")
- 10 ml of absolute tetrahydrofuran The crude product obtained is chromatographed over a silica gel column (silica gel 60-Merck, particle size: 0.04 to 0.063 mm), eluting first with methylenechloride and then with cyclohexane:acetone (4:1). 53.9 mg (13.0% of theory) of cyclo(-N-methyl-L-leucinyl-D-thio-lactyl-N-methyl-L-leucinyl-D-4-(pyrid-2-yl-methoxy)-phenyllactyl-N-methyl-L-leucinyl-D-lactyl-N-methyl-L-leucinyl-D-4-(pyrid-2-yl-methoxy)-phenyllactyl-) are obtained.

$^{13}$C NMR (CDCl$_3$, δ): 204.9; 205.8 ppm (—NMe-$\underline{C}$=S)/2 confirmational isomers.

LC-MS (loop) m/z (%): 1179 (M$^+$, 100).

$C_{64}H_{86}N_6O_{13}S$ (1179.5)

Example 12

Cyclo(-N-methyl-L-leucinyl-D-thiolactyl-N-methyl-L-leucinyl-D-4-(fur-2-yl-methoxy)-phenyllactyl-N-methyl-L-leucinyl-D-lactyl-N-methyl-L-leucinyl-D-4-(fur-2-yl-methoxy)-phenyllactyl-)

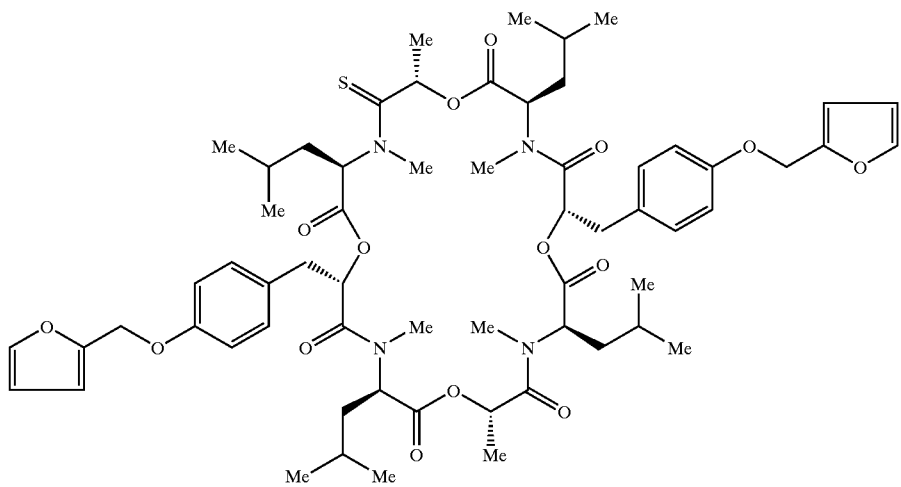

The thionation is carried similarly to the reaction procedure of Example 9, using:

- 0.47 g (0.41 mmol) of cyclo(-N-methyl-L-leucinyl-D-lactyl-N-methyl-L-leucinyl-D-4-(fur-2-yl-methoxy)-phenyllactyl-N-methyl-L-leucinyl-D-lactyl-N-methyl-L-leucinyl-D-4-(fur-2-yl-methoxy)-phenyllactyl-) (cf. WO 97/11 064)
- 0.20 g (0.41 mmol) of 2,4-bis-(4-phenoxy-phenyl)-2,4-dithioxo-1,3,2,4-dithiadiphosphetan ("Belleau's Reagent")
- 10 ml of absolute tetrahydrofuran The crude product obtained is chromatographed over a silica gel column (silica gel 60-Merck, particle size: 0.04 to 0.063 mm), eluting first with methylenechloride and then with cyclohexane:acetone (4:1). 130 mg (27.3% of theory) of cyclo(-N-methyl-L-leucinyl-D-thio-lactyl-N-methyl-L-leucinyl-D-4-(fur-2-yl-methoxy)-phenyllactyl-N-methyl-L-leucinyl-D-lactyl-N-methyl-L-leucinyl-D-4-(fur-2-yl-methoxy)-phenyllactyl-) are obtained.

$^{13}$C NMR (CDCl$_3$, δ): 204.9: 205.8 ppm (—NMe-$\underline{C}$=S)/2 confirmational isomers.

LC-MS (acidic) m/z (%): 1158 (M+H, 100).

$C_{62}H_{84}N_4O_{15}S$ (1157.4)

R$_t$ (HPLC): 17.85 min.

Example 13

Cyclo(N-methyl-L-leucinyl-D-thiolactyl-N-methyl-L-leucinyl-D-4-(fur-2-yl-methoxy)-phenyllactyl-N-methyl-L-leucinyl-D-lactyl-N-methyl-L-leucinyl-D-phenyllactyl-)

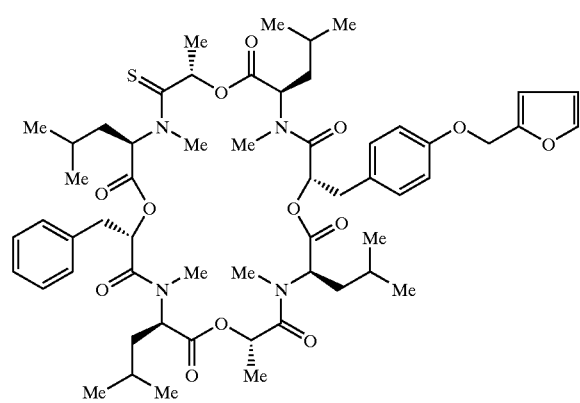

The thionation is carried out similarly to the reaction procedure of Example 9, using:

- 0.40 g (0.38 mmol) of cyclo(-N-methyl-L-leucinyl-D-lactyl-N-methyl-L-leucinyl-D-4-(fur-2-yl-methoxy)-phenyllactyl-N-methyl-L-leucinyl-D-lactyl-N-methyl-L-leucinyl-D-phenyllactyl-) (cf. WO 97/11 064)
- 0.20 g (0.38 mmol) of 2,4-bis-(4-phenoxy-phenoyl)2,4-dithioxo-1,3,2,4-dithiadiphosphetan ("Belleau's Reagent")
- 10 ml of absolute tetrahydrofuran The crude product obtained is chromatographed over a silica gel column (silica gel 60-Merck, particle size: 0.04 to 0.063 mm), eluting first with (methylenechloride and then with cyclohexane:acetone (4:1). 46.1 mg (11.4% of theory) of cyclo(N-methyl-L-leucinyl-D-thiolactyl-N-methyl-L-leucinyl-D-4-(fur-2yl-methoxy)-phenyllactyl-N-methyl-L-leucinyl-D-lactyl-N-methyl-L-leucinyl-D-phenyllactyl-) are obtained.

LC-MS (loop) m/z (%): 1061 (M$^+$, 100).

$C_{57}H_{80}O_{13}S$ (1061.3)

$R_t$ (HPLC): 17.55 min.

The insecticidal and acaricidal activity of the compounds which can be used according to the invention is demonstrated by the examples below. In these examples, active compounds from the table below are used:

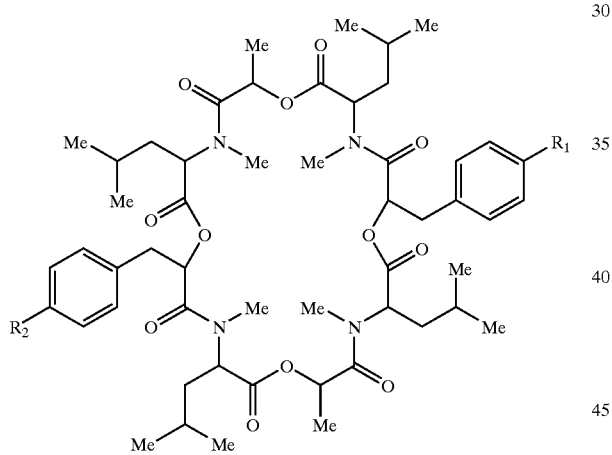

| Comp.-No.*) | R$^1$ | R$^2$ |
|---|---|---|
| 14 | morpholinomethoxy | morpholinomethoxy |
| 15 | pyrrolidinyl-methoxy | —H |
| 16 | furyl-methoxy | —H |
| 17 | furyl-methoxy | furyl-methoxy |
| 18 | pyridyl-methoxy | pyridyl-methoxy |

*)Ex. 14: cf. WO 93/19 053; EP-A 634 408 Ex. 15, 16, 17, 18: cf. WO 97/11 064

Example A

Blowfly Larvae Test/Development-inhibitory Action

Test animals: *Lucilia cuprina* larvae (1st–3rd stage)

Solvent: Dimethyl sulphoxide 20 mg of active compound are dissolved in one ml of dimethyl sulphoxide. To prepare a suitable formulation, the solution of active compound is diluted with water to the particular desired concentration.

About 20 *Lucilia cuprina* larvae are introduced into a test tube which contains about 1 cm$^3$ of horse meat and 0.5 ml of the preparation of active compound to be tested. After 24 hours and 48 hours, the effectiveness of the preparation of active compound is determined. The test tubes are transferred into beakers whose bottom is covered with sand. After a further two days, the test tubes are removed and the pupae are counted.

The effect of the preparation of active compound is assessed by the number of flies which have hatched after 1.5 times the development period of an untreated control. 100% means that no flies have hatched; 0% means that all flies have hatched normally.

In this test, for example, the following compounds of the preparation examples show superior activity compared to the prior art:

| Prior art | | | According to the invention | | |
|---|---|---|---|---|---|
| Depsi-peptide | Dosage (in ppm) | Activity (in %) | Comp. No. | Dosage (in ppm) | Activity (in %) |
| PF 1022A | 1000 | 0 | 9 | 1000 | 100 |
| | | | 9 | 100 | 100 |
| | | | 14 | 1000 | 100 |
| | | | 14 | 100 | 100 |
| | | | 15 | 1000 | 100 |
| | | | 16 | 1000 | 100 |
| | | | 17 | 1000 | 100 |
| | | | 17 | 100 | 100 |
| | | | 18 | 1000 | 100 |
| | | | 18 | 100 | 100 |

Example B

Test with Resistant Monoxenous Cattle Ticks/SP-resistant Parkhurst Strain

Test animals: Adult females of *Boophilus microplus* (parkhurst strain, SP-resistant) which have sucked themselves full Solvent: Dimethyl sulphoxide 20 mg of active compound are dissolved in one ml of dimethyl sulphoxide, more dilute concentrations are prepared by dilution in the same solvent.

The test is carried out in five replications. 1 μl of the solutions is injected into the abdomen, and the animals are transferred into dishes and kept in a climatized room. After seven days, the activity is checked by examination for the position of fertile eggs. Eggs whose fertility is not visible from the outside are stored in glass tubes in a controlled-environment cabinet until the larvae have hatched after about 24 days. An activity of 100% means that the tick has not produced any fertile eggs.

In this test, for example, the following compounds of the preparation examples show an activity which is superior to the prior art.

| Prior art | | | According to the invention | | |
|---|---|---|---|---|---|
| Depsi-peptide | Dosage (in μg) | Activity (in %) | Comp. No. | Dosage (in μg) | Activity (in %) |
| PF 1022A | 20 | 0 | 14 | 20 | 100 |

Example C

Test with Cat Fleas/oral Uptake

Test animals: Adults of *Ctenocephalides felis*

Solvent: Dimethyl sulphoxide (DMSO)

To produce a suitable formulation, a suitable solution of active compound is prepared from 20 mg of active compound and 1 ml of DMSO. 7.5 μl of this formulation are added to 3.5 ml of citrated cattle blood and stirred.

20 unfed adult fleas (*Ctenocephalides felis*, strain "Georgi") are placed into a chamber (Ø 2.5 cm) whose top and bottom are closed with gauze. A metal cylinder whose underside is covered with parafilm is placed onto the chamber. The cylinder contains 3 ml of blood/active compound formulation which can be taken up by the fleas through the parafilm membrane. Whereas the blood is warmed to 37° C., the temperature in the area of the flea chambers is adjusted to 25° C. Controls are mixed with the same volume of DMSO, without addition of a compound. The determinations are carried out in triplicate.

After 24 h, the mortality in % (=dead fleas) is determined, using imidacloprid as standard.

Compounds which effect the kill of the fleas of at least 24% within 24 h are judged to be effective.

| Prior art | | | According to the invention | | |
|---|---|---|---|---|---|
| Depsi-peptide | Dosage (in μg) | Activity (in %) | Comp. No. | Dosage (in μg) | Activity (in %) |
| PF 1022A | 100 | 0 | 9 | 100 | 100 |
| | | | 14 | 100 | 90 |
| | | | 18 | 100 | 100 |

Example D

In vivo Test on Ticks/mini-dip on Cattle

Test object: All stages of *Boophilus microplus* (larvae, metalarvae, nymphs, metanymphs and adults) pyrethroid-resistant strain.

Solution: Active compound 30% strength in methyl glycol and emulsifier NP 10 in a ratio of 1:1.

For the treatment of the cattle, concentrations of 1000, 300, 100, 30, 10 and 1 ppm are used, in a volume of 200 ml. The cattle hide to be treated is wetted with the solution of active compound for 1 min.

14×, in intervals of two days, cattle is infected with about 3000 14- to 28-day-old larvae of B. microplus which have not been fed. On day 23 p.i., defined areas on the surface of the cattle skin are wetted with the abovementioned preparation of active compound. From day 24 to 45 p.i., the female adult ticks which develop are counted, and the fertility of the eggs laid by these ticks is checked and used to determine the activity of the preparation of active compound. 100% means that no ticks with fertile eggs were found; 0% means that the number of ticks and the fertility of the eggs laid was comparable to that of control.

In this test, the compounds 14, 15, 16 and 18 show an activity of 100% against B, microplus on cattle at active compound concentrations of 1000 ppm.

| Prior art | | | According to the invention | | |
|---|---|---|---|---|---|
| Depsi-peptide | Dosage (in μg) | Activity (in %) | Comp. No. | Dosage (in μg) | Activity (in %) |
| PF 1022A | 1000 | 0 | 14 | 1000 | 100 |
| | | | 15 | 1000 | 100 |
| | | | 16 | 1000 | 100 |
| | | | 18 | 1000 | 100 |

What is claimed is:

1. A method of inhibiting proliferation of ectoparasites on animals comprising contacting the ectoparasites with a cyclooctadepsipeptide of the formula (I)

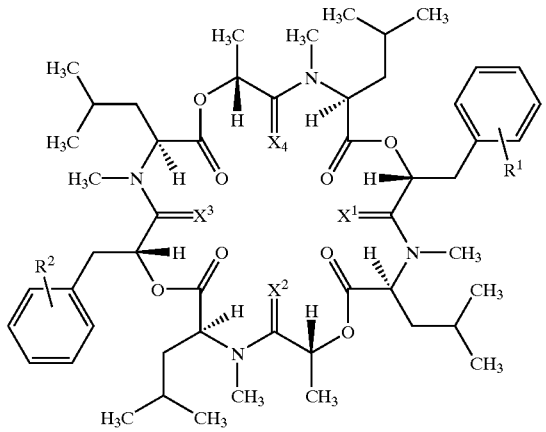

in which

R$^1$ represents hydrogen, C$_{1-4}$-alkyl, hydroxyl, halogen, C$_{1-4}$-alkoxy, C$_{1-4}$-alkoxy-C$_{1-4}$-alkyl, heterocyclylmethyl, R$^2$ represents hydrogen, C$_{1-4}$-alkyl, hydroxyl, halogen, C$_{1-4}$-alkoxy, C$_{1-4}$-alkoxy-C$_{1-4}$alkyl, heterocyclylmethyl, X$^1$, X$^2$, X$^3$ and X$^4$ independently of one another represent oxygen or sulfur, where, if R$^1$ and R$^2$ simultaneously represent hydrogen, at least one of the radicals X$^1$, X$^2$, X$^3$ and X$^4$ represents sulfur, for a time and under a condition effective to inhibit proliferation of said ectoparasites.

2. A composition comprising a suitable carrier and a cyclic depsipeptide of the formula (I)

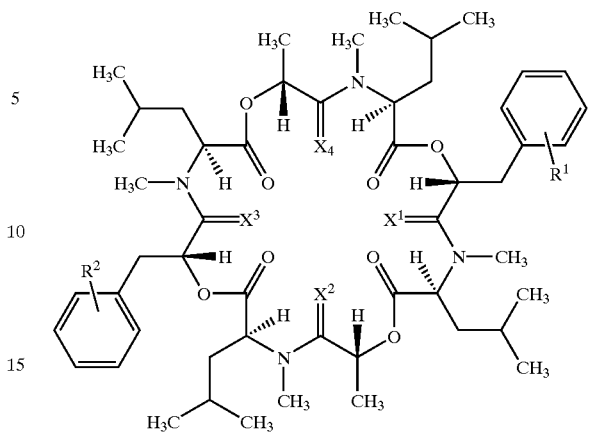

in which

R$^1$ represents hydrogen, C$_{1-4}$-alkyl, hydroxyl, halogen, C$_{1-4}$-alkoxy, C$_{1-4}$-alkoxy-C$_{1-4}$-alkyl, heterocyclylmethyl, R$^2$ represents hydrogen, C$_{1-4}$-alkyl, hydroxyl, halogen, C$_{1-4}$-alkoxy, C$_{1-4}$-alkoxy-C$_{1-4}$-alkyl, heterocyclylmethyl, X$^1$, X$^2$, X$^3$ and X$^4$ independently of one another represent oxygen or sulfur, wherein at least one of the radicals X$^1$, X$^2$, X$^3$ and X$^4$ represents sulfur.

3. The method of claim 1 wherein R$^1$ represents pyridylmethyl, tetrahydrofuranylmethyl, pyrrolidinylmethyl, furylmethyl, thienylmethyl, or heteroarhyl-C$_{1-2}$-alkoxy.

4. The method of claim 1 wherein R$^1$ represents pyridyl-methoxy, tetrahydrofuryl-methoxy, pyrrolidinyl-methoxy, furyl-methoxy, nitro, —NR$^3$R$^4$, or —SO$_2$—NR$^3$R$^4$.

5. The method of claim 1 wherein R$^2$ represents pyridylmethyl, tetrahydrofuranylmethyl, pyrrolidinylmethyl, furylmethyl, thienylmethyl, or heteroaryl-C$_{1-2}$-alkoxyl.

6. The method of claim 1 wherein R$^2$ represents pyridyl-methoxy, tetrahydrofuranyl-methoxy, pyrrolidinyl-methoxy, furyl-methoxy, nitro, —NR$^3$R$^4$, or —SO$_2$—NR$^3$R$^4$.

7. The method of claim 1 wherein R$^3$ and R$^4$ independently of one another each represents benzyl, or heterocyclylmethyl.

8. The method of claim 1 wherein R$^3$ and R$^4$ independently of one another each represents pyridylmethyl, tetrahydrofuranylmethyl, pyrrolidinylmethyl, furylmethyl, or thienylmethyl.

* * * * *